US012642570B2

(12) United States Patent
Bar-Tal et al.

(10) Patent No.: US 12,642,570 B2
(45) Date of Patent: Jun. 2, 2026

(54) ABLATION CATHETER WITH STRAIN GAUGES

(71) Applicant: Biosense Webster (Israel) Ltd., Yokneam (IL)

(72) Inventors: Meir Bar-Tal, Haifa (IL); Avi Reuveni, Givat Shmuel (IL); Eran Yona Hirszowicz, Ramat Gan (IL); Stav Abi Hirszowicz, Ramat Gan (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 208 days.

(21) Appl. No.: 15/262,726

(22) Filed: Sep. 12, 2016

(65) Prior Publication Data

US 2018/0071009 A1 Mar. 15, 2018

(51) Int. Cl.
*A61B 18/12* (2006.01)
*A61B 5/00* (2006.01)
(Continued)

(52) U.S. Cl.
CPC ............ *A61B 18/12* (2013.01); *A61B 5/6885* (2013.01); *A61B 18/14* (2013.01); *A61B 18/1492* (2013.01); *A61B 2018/00011* (2013.01); *A61B 2018/00029* (2013.01); *A61B 2018/00351* (2013.01); *A61B 2018/00577* (2013.01);
(Continued)

(58) Field of Classification Search
CPC ................ A61B 18/1492; A61B 18/14; A61B 2090/064; A61B 5/6885; A61B 18/082;

A61B 18/12; A61B 2018/00011; A61B 2018/00029; A61B 2018/00351; A61B 2018/00577; A61B 2018/00601;
(Continued)

(56) References Cited

U.S. PATENT DOCUMENTS 4,407,686 A * 10/1983 Cook .................... G01L 1/2287
156/215
5,329,923 A * 7/1994 Lundquist .......... A61B 18/1492
600/373
(Continued)

FOREIGN PATENT DOCUMENTS

| CN | 1430488 A | 7/2003 |
| CN | 102341053 A | 2/2012 |

(Continued)

OTHER PUBLICATIONS

Extended European Patent Search Report for corresponding European Patent Application EP 17190325.5, dated Jan. 29, 2018.
(Continued)

*Primary Examiner* — Eun Hwa Kim
*Assistant Examiner* — Catherine C. Premraj
(74) *Attorney, Agent, or Firm* — FBT Gibbons LLP

(57) ABSTRACT

Described embodiments include apparatus that includes a catheter. A tube, at a distal portion of the catheter, includes a plurality of segments that are at least partly disconnected from each other, and a plurality of bridges that span respective neighboring pairs of the segments. The apparatus further includes one or more strain gauges, each of the strain gauges being coupled to a respective one of the bridges, and being configured to output a signal in response to bending of the respective one of the bridges. Other embodiments are also described.

19 Claims, 4 Drawing Sheets

(51) Int. Cl.

| | |
|---|---|
| *A61B 18/14* | (2006.01) |
| *A61B 18/00* | (2006.01) |
| *A61B 18/08* | (2006.01) |
| *A61B 90/00* | (2016.01) |

(52) U.S. Cl.
CPC ............... *A61B 2018/00601* (2013.01); *A61B 2018/00791* (2013.01); *A61B 2018/00839* (2013.01); *A61B 18/082* (2013.01); *A61B 2090/064* (2016.02); *A61B 2562/0261* (2013.01)

(58) Field of Classification Search
CPC ........... A61B 2018/00791; A61B 2018/00839; A61B 2562/0261
See application file for complete search history.

(56) References Cited

U.S. PATENT DOCUMENTS

| | | | |
|---|---|---|---|
| 5,643,197 A | 7/1997 | Brucker et al. | |
| 5,697,927 A | 12/1997 | Imran et al. | |
| 6,733,457 B2 | 5/2004 | Flesch et al. | |
| 8,147,486 B2 | 4/2012 | Honour et al. | |
| 8,529,476 B2 | 9/2013 | Govari | |
| 9,039,700 B2 | 5/2015 | Kirschenman et al. | |
| 10,973,572 B2 | 4/2021 | Datta et al. | |
| 11,555,349 B2 | 1/2023 | Lagarde | |
| 11,559,349 B2 | 1/2023 | Bar-tal et al. | |
| 2005/0055019 A1 | 3/2005 | Skarda | |
| 2007/0219551 A1* | 9/2007 | Honour | A61B 5/0422 606/41 |
| 2008/0009750 A1 | 1/2008 | Aeby | |
| 2008/0147060 A1 | 6/2008 | Choi | |
| 2008/0294158 A1 | 11/2008 | Pappone et al. | |
| 2009/0099551 A1 | 4/2009 | Tung | |
| 2009/0143651 A1 | 6/2009 | Kallback et al. | |
| 2009/0157092 A1* | 6/2009 | Blumenkranz | G01L 1/246 73/800 |
| 2010/0063478 A1* | 3/2010 | Selkee | A61B 18/1492 604/524 |
| 2010/0099951 A1* | 4/2010 | Laby | A61B 1/00045 600/144 |
| 2010/0191175 A1 | 7/2010 | Couvillon, Jr. | |
| 2011/0160726 A1 | 6/2011 | Ingle | |
| 2011/0172658 A1 | 7/2011 | Gelbart et al. | |
| 2011/0282342 A1 | 11/2011 | Leo et al. | |
| 2012/0165809 A1* | 6/2012 | Christian | A61B 18/1492 606/41 |
| 2012/0265102 A1 | 10/2012 | Leo | |
| 2013/0030426 A1 | 1/2013 | Gallardo et al. | |
| 2013/0090652 A1* | 4/2013 | Jenson | A61B 18/1492 606/41 |
| 2013/0123775 A1* | 5/2013 | Grunewald | A61B 18/1492 606/41 |
| 2013/0150693 A1 | 6/2013 | D'Angelo et al. | |
| 2013/0231657 A1* | 9/2013 | Datta | A61B 18/1492 606/41 |
| 2014/0024970 A1* | 1/2014 | Govari | A61B 18/1492 600/587 |
| 2014/0058375 A1* | 2/2014 | Koblish | A61B 18/18 606/33 |
| 2014/0171937 A1* | 6/2014 | Morris | A61B 18/1206 606/34 |
| 2014/0276052 A1* | 9/2014 | Rankin | A61B 18/1492 600/439 |
| 2014/0276078 A1* | 9/2014 | Schweitzer | A61B 5/283 600/459 |
| 2015/0105701 A1 | 4/2015 | Mayer et al. | |
| 2015/0272669 A1 | 10/2015 | Brucker et al. | |
| 2016/0113712 A1 | 4/2016 | Cheung et al. | |
| 2016/0128765 A1 | 5/2016 | Schultz et al. | |
| 2016/0183821 A1 | 6/2016 | Pai et al. | |
| 2018/0071009 A1 | 3/2018 | Bar-Tal et al. | |
| 2018/0071016 A1 | 3/2018 | Bar-Tal et al. | |
| 2019/0307504 A1 | 10/2019 | Shen et al. | |
| 2024/0122642 A1 | 4/2024 | Bar-Tal et al. | |
| 2024/0189026 A1 | 6/2024 | Bar-Tal et al. | |

FOREIGN PATENT DOCUMENTS

| | | |
|---|---|---|
| CN | 102631240 A | 8/2012 |
| CN | 105050523 A | 11/2015 |
| CN | 204744408 U | 11/2015 |
| CN | 105188588 A | 12/2015 |
| CN | 105473091 A | 4/2016 |
| CN | 105496548 A | 4/2016 |
| CN | 205234628 U | 5/2016 |
| CN | 105726118 A | 7/2016 |
| EP | 2564801 A1 | 3/2013 |
| EP | 3020355 A1 | 5/2016 |
| EP | 3178428 A1 | 6/2017 |
| EP | 3292831 A1 | 3/2018 |
| EP | 3292832 A1 | 3/2018 |
| EP | 3292833 A1 | 3/2018 |
| EP | 3492033 A1 | 6/2019 |
| JP | H07-255855 A | 10/1995 |
| JP | 2007-289389 A | 11/2007 |
| JP | 2014-506169 A | 3/2014 |
| JP | 2014-161452 A | 9/2014 |
| WO | 2010/088922 A1 | 8/2010 |
| WO | WO 2012/091793 A1 | 7/2012 |
| WO | 2012/173673 A1 | 12/2012 |
| WO | WO 2014/124231 A1 | 8/2014 |
| WO | 2014/151822 A2 | 9/2014 |
| WO | 2015/194597 A1 | 12/2015 |
| WO | WO 2016/065337 A1 | 4/2016 |

OTHER PUBLICATIONS

European Search Report and Written Opinion dated Jan. 31, 2018 for Application No. 17190379.2, 9 pages.

European Search Report and Written Opinion dated Feb. 1, 2018 for Application No. 17190450.1, 7 pages.

European Communication dated Mar. 19, 2021, for Application No. 17190379.2, 4 pages.

European Communication dated Jul. 19, 2021, for Application No. 17190325.5, 4 pages.

European Communication dated Aug. 9, 2021, for Application No. 17190450.1, 4 pages.

Japanese Notification of Reasons for Refusal dated Jun. 29, 2021, for Application No. 2017-173749, 4 pages.

Japanese Notification of Reasons for Refusal dated Jun. 29, 2021, for Application No. 2017-173754, 5 pages.

Japanese Notification of Reasons for Refusal dated Jun. 29, 2021, for Application No. 2017-173757, 4 pages.

Chinese First Office Action and Search Report dated Oct. 9, 2021, for Application No. 201710815768.8, 10 pages.

Chinese Final Office Action dated Apr. 13, 2022, for Application No. 201710815768.8, 8 pages.

Chinese First Office Action and Search Report dated Nov. 1, 2021, for Application No. 201710817244.2, 6 pages.

Chinese Second Office Action and Search Report dated Jul. 18, 2022, for Application No. 201710817244.2, 7 pages.

Chinese Third Office Action dated Dec. 16, 2022, for Application No. 201710817244.2, 6 pages.

Chinese First Office Action and Search Report dated Nov. 2, 2021, for Application No. 201710818151.1, 6 pages.

Chinese Second Office Action and Search Report dated Jul. 18, 2022, for Application No. 201710818151.1, 7 pages.

Chinese Third Office Action dated Dec. 16, 2022, for Application No. 201710818151.1, 5 pages.

Chinese Final Office Action dated Apr. 28, 2023, for Application No. 201710818151.1, 11 pages.

European Extended Search Report and Written Opinion dated Jan. 5, 2023, for Application No. 22200899.7, 8 pages.

European Extended Search Report and Written Opinion dated Feb. 26, 2024, for Application No. 23212586.4, 8 pages.

(56) References Cited

OTHER PUBLICATIONS

European Communication dated Feb. 3, 2025, for Application No. 23212586.4, 5 pages.

Japanese Final Office Action dated Mar. 15, 2022, for Application No. 2017-173754, 2 pages.

Chinese Notice of Reexamination dated Apr. 15, 2025, for Application No. 201710815768.8, 7 pages.

European Summons to Attend Oral Proceedings dated Feb. 19, 2024, for Application No. 17190325.5, 8 pages.

European Summons to Attend Oral Proceedings dated Nov. 15, 2024, for Application No. 17190325.5, 11 pages.

Japanese First Office Action dated Mar. 14, 2023, for Application No. 2022-078706, 3 pages.

* cited by examiner

ABLATION CATHETER WITH STRAIN GAUGES

CROSS-REFERENCE TO RELATED APPLICATIONS

The present application is related to an application entitled "Ablation catheter with a flexible printed circuit board," filed on even date herewith, and to an application entitled "Irrigation system for a catheter," filed on even date herewith.

FIELD OF THE INVENTION

Embodiments of the present invention are related generally to the field of medical devices, and specifically to catheters for ablation procedures.

BACKGROUND

In some ablation procedures, a catheter is inserted into a heart, and an ablation electrode at the distal end of the catheter is used to deliver an ablating signal to the tissue.

US Patent Application Publication 2013/0030426, whose disclosure is incorporated herein by reference, describes a catheter adapted for ablation having multiple dedicated irrigation tubings to supply fluid to their respective electrode or set of electrodes. The tubings provide parallel flow pathways through the catheter where irrigation fluid is delivered to irrigated tip and/or ring electrodes which can accomplish uni-polar or bi-polar ablation. Such separate and dedicated fluid pathways allow fluid to be delivered to the corresponding electrode or set of electrodes at different flow rates. An integrated ablation system using such catheter has an ablation energy source and an irrigation pump with multiple pump heads that can operate independently of each other. An integrated irrigation tubing set is included to extend between the fluid source and the catheter, with each pump head being able to act on a different tubing that delivers fluid to a different electrode or set of electrodes.

U.S. Pat. No. 8,147,486, whose disclosure is incorporated herein by reference, describes a catheter or lead having a flexible printed circuit for conveying signals and/or energy. Each trace may be in electrical connection with one or more external electrical contacts. More specifically, each trace is typically electrically connected to a single contact. The traces and contacts may assist in diagnosis and/or detection of bio-electrical signals emitted by organs, and may transmit such signals to a connector or diagnostic device affixed to the catheter. The external electrical contacts may detect bioelectric energy or may deliver electrical or thermal energy to a target site.

PCT Application Publication WO 2014/124231, whose disclosure is incorporated herein by reference, describes a flex-PCB catheter device that is configured to be inserted into a body lumen. The flex-PCB catheter comprises an elongate shaft, an expandable assembly, a flexible printed circuit board (flex-PCB) substrate, a plurality of electronic components and a plurality of communication paths. The elongate shaft comprises a proximal end and a distal end. The expandable assembly is configured to transition from a radially compact state to a radially expanded state. The plurality of electronic elements are coupled to the flex-PCB substrate and are configured to receive and/or transmit an electric signal. The plurality of communication paths are positioned on and/or within the flex-PCB substrate. The communication paths selectively couple the plurality of electronic elements to a plurality of electrical contacts configured to electrically connect to an electronic module configured to process the electrical signal. The flex-PCB substrate can have multiple layers, including one or more metallic layers. Acoustic matching elements and conductive traces can be includes in the flex-PCB substrate.

U.S. Pat. No. 8,529,476, whose disclosure is incorporated herein by reference, describes a medical probe, including a flexible insertion tube, having a distal end for insertion into a body cavity of a patient and which is configured to be brought into contact with tissue in the body cavity. The probe further includes a sensor tube of an elastic material, contained inside the distal end of the insertion tube and configured to deform in response to forces exerted by the tissue on the distal end. The probe also includes a plurality of strain gauges fixedly attached to a surface of the sensor tube at different, respective locations and configured to generate respective signals in response to deformations of the sensor tube.

SUMMARY OF THE INVENTION

There is provided, in accordance with some embodiments of the present invention, apparatus, including:

a catheter;

a tip electrode, at a distal end of the catheter, shaped to define a plurality of microelectrode apertures;

at least one printed circuit board (PCB) disposed within a lumen of the catheter; and a plurality of microelectrodes coupled to the PCB and at least partly situated within the microelectrode apertures, the PCB being configured to carry signals from the microelectrodes.

In some embodiments, each of the microelectrodes includes:

a conducting element; and an isolating wall that electrically- and thermally-isolates the conducting element from the tip electrode.

In some embodiments, the apparatus further includes a plurality of temperature sensors coupled to the PCB, each of the temperature sensors being thermally coupled to the conducting element of a respective one of the microelectrodes.

In some embodiments, the microelectrodes are fittingly situated within the microelectrode apertures.

In some embodiments, the microelectrodes are fixed to respective perimeters of the microelectrode apertures.

In some embodiments, the apparatus further includes a catheter handle at a proximal end of the catheter, wherein the PCB is coupled to the catheter handle.

In some embodiments, the apparatus further includes a structure disposed within a lumen of the tip electrode and configured to inhibit retraction of the microelectrodes through the microelectrode apertures by supporting the PCB.

In some embodiments, a distal end of the structure is positioned within 0.1 mm of a distal face of the tip electrode.

In some embodiments, the structure is annular.

In some embodiments, the tip electrode is further shaped to define a plurality of fluid apertures configured to allow passage of a fluid therethrough.

In some embodiments, the PCB is positioned within a lumen of the tip electrode such as to define a space, between the PCB and an inner surface of the tip electrode, for passage of the fluid to the fluid apertures.

In some embodiments, the space is less than 0.3 mm in a radial direction.

In some embodiments, at least some of the microelectrodes are located along a distal face of the tip electrode.

In some embodiments, the at least some of the microelectrodes that are located along the distal face of the tip electrode are oriented obliquely with respect to the distal face of the tip electrode.

In some embodiments, at least some of the microelectrodes are located along a circumferential face of the tip electrode.

There is further provided, in accordance with some embodiments of the present invention, a method, including:
using a tip electrode at a distal end of a catheter, passing an ablating signal into tissue;
using a plurality of microelectrodes that are coupled to at least one printed circuit board (PCB) within a lumen of the catheter, and are at least partly situated within a plurality of microelectrode apertures in the tip electrode, acquiring signals from the tissue; and
using the PCB, carrying the signals, and anchoring the tip electrode to a handle of the catheter.

In some embodiments, the method further includes, while passing the ablating signal into the tissue, passing a fluid through a plurality of fluid apertures in the tip electrode.

In some embodiments, passing the fluid through the fluid apertures includes passing the fluid through the fluid apertures via a space between the PCB and the tip electrode.

In some embodiments, passing the fluid through the fluid apertures includes passing the fluid through the fluid apertures via a conduit that is supporting the PCB.

In some embodiments, the method further includes measuring a temperature of the tissue, using a plurality of temperature sensors that are thermally coupled to respective conducting elements of the microelectrodes.

There is further provided, in accordance with some embodiments of the present invention, apparatus, including:
a catheter;
a tube, at a distal portion of the catheter, including a plurality of segments that are at least partly disconnected from each other, and a plurality of bridges that span respective neighboring pairs of the segments; and
one or more strain gauges, each of the strain gauges being coupled to a respective one of the bridges, and being configured to output a signal in response to bending of the respective one of the bridges.

In some embodiments, each of the strain gauges is coupled to an outer surface of the respective one of the bridges.

In some embodiments, each of the strain gauges is coupled to an inner surface of the respective one of the bridges.

In some embodiments, the tube is shaped to define one or more slots at respective longitudinal positions along the tube, each of the slots separating between a respective pair of the segments.

In some embodiments, each of the slots includes a circumferential portion that passes circumferentially along the tube, and two longitudinal portions that pass longitudinally along the tube at respective ends of the circumferential portion, and a respective one of the bridges is between the two longitudinal portions of the slot.

In some embodiments, each of the slots is, circumferentially, between 315 and 345 degrees long.

In some embodiments, the apparatus further includes a tip electrode at a distal end of the catheter, the tube being electrically coupled to the tip electrode.

In some embodiments, the tip electrode and the tube are formed of a single piece of material.

In some embodiments, the tube is metallic.

In some embodiments, the apparatus further includes at least one printed circuit board (PCB) disposed within the tube and configured to carry the signals from the strain gauges.

In some embodiments, the strain gauges are mounted on the PCB.

In some embodiments, the apparatus further includes a structure that supports the PCB, the structure being coupled to the tube.

In some embodiments, the structure includes a plurality of tabs, and the structure is coupled to the tube by virtue of the tabs fitting into complementary apertures in the tube.

In some embodiments, the structure includes a conduit configured to allow passage of a fluid therethrough.

In some embodiments, the strain gauges include three strain gauges disposed at different respective circumferential positions along the tube.

There is further provided, in accordance with some embodiments of the present invention, a method, including:
using a tip electrode at a distal end of a catheter, passing an ablating signal into tissue,
the catheter including a tube that includes a plurality of segments that are at least partly disconnected from each other, and a plurality of bridges that span respective neighboring pairs of the segments; and
while passing the ablating signal into the tissue, estimating a force applied to the tissue by the catheter, using a plurality of strain gauges coupled to the bridges.

In some embodiments, the method further includes, while passing the ablating signal into the tissue, passing a fluid through a plurality of fluid apertures in the tip electrode.

In some embodiments, the passing the fluid through the plurality of fluid apertures includes passing the fluid through the plurality of fluid apertures via the tube.

In some embodiments, estimating the force includes:
using the strain gauges, outputting signals in response to bending of the bridges, and
based on the signals, estimating the force.

In some embodiments, the method further includes, using a printed circuit board (PCB) disposed within a lumen of the catheter, carrying the signals to a proximal end of the catheter.

There is further provided, in accordance with some embodiments of the present invention, apparatus, including:
a catheter;
a tip electrode, at a distal end of the catheter, shaped to define a plurality of fluid apertures; and
a structure, within the tip electrode, configured such that fluid passed distally through a lumen of the catheter flows in a longitudinal direction through a space between the structure and an inner surface of the tip electrode, prior to exiting through the fluid apertures.

In some embodiments, the structure is configured such that fluid flows through the space in a distal direction.

In some embodiments, the structure is configured such that the fluid flows through the space in a proximal direction.

In some embodiments, the structure includes a conduit.

In some embodiments, the conduit is configured such that the fluid exits a distal opening of the conduit, and is then deflected into the space by a distal face of the tip electrode.

In some embodiments, a majority of the fluid apertures are in a circumferential face of the tip electrode.

In some embodiments, the distal opening of the conduit is positioned within 0.3 mm of the distal face of the tip electrode.

In some embodiments, the structure is shaped to define one or more circumferential openings, such that the fluid flows into the space through the circumferential openings.

In some embodiments, the space is less than 0.3 mm in a radial direction.

In some embodiments, at least part of the space is less than 0.1 mm in a radial direction.

There is further provided, in accordance with some embodiments of the present invention, a method, including:

using a tip electrode at a distal end of a catheter, passing an ablating signal into tissue; and while passing the ablating signal into the tissue, causing fluid to flow in a longitudinal direction through a space between a structure and an inner surface of the tip electrode, and to subsequently exit the tip electrode through fluid apertures in the tip electrode.

In some embodiments, causing the fluid to flow in the longitudinal direction includes causing the fluid to flow in a distal direction.

In some embodiments, causing the fluid to flow in the longitudinal direction includes causing the fluid to flow in a proximal direction.

In some embodiments, the structure includes a conduit, and the method further includes causing the fluid to flow through the conduit prior to flowing through the space.

In some embodiments, the method further includes causing the fluid to exit a distal opening of the conduit, and to be deflected into the space by a distal face of the tip electrode.

In some embodiments, the distal opening of the conduit is positioned within 0.3 mm of the distal face of the tip electrode.

In some embodiments, the method further includes causing the fluid to flow into the space through one or more circumferential openings in the structure.

In some embodiments, a majority of the fluid apertures are in a circumferential face of the tip electrode.

In some embodiments, the space is less than 0.3 mm in a radial direction.

In some embodiments, at least part of the space is less than 0.1 mm in a radial direction.

The present invention will be more fully understood from the following detailed description of embodiments thereof, taken together with the drawings, in which:

DETAILED DESCRIPTION OF EMBODIMENTS

Overview

Figure 1:
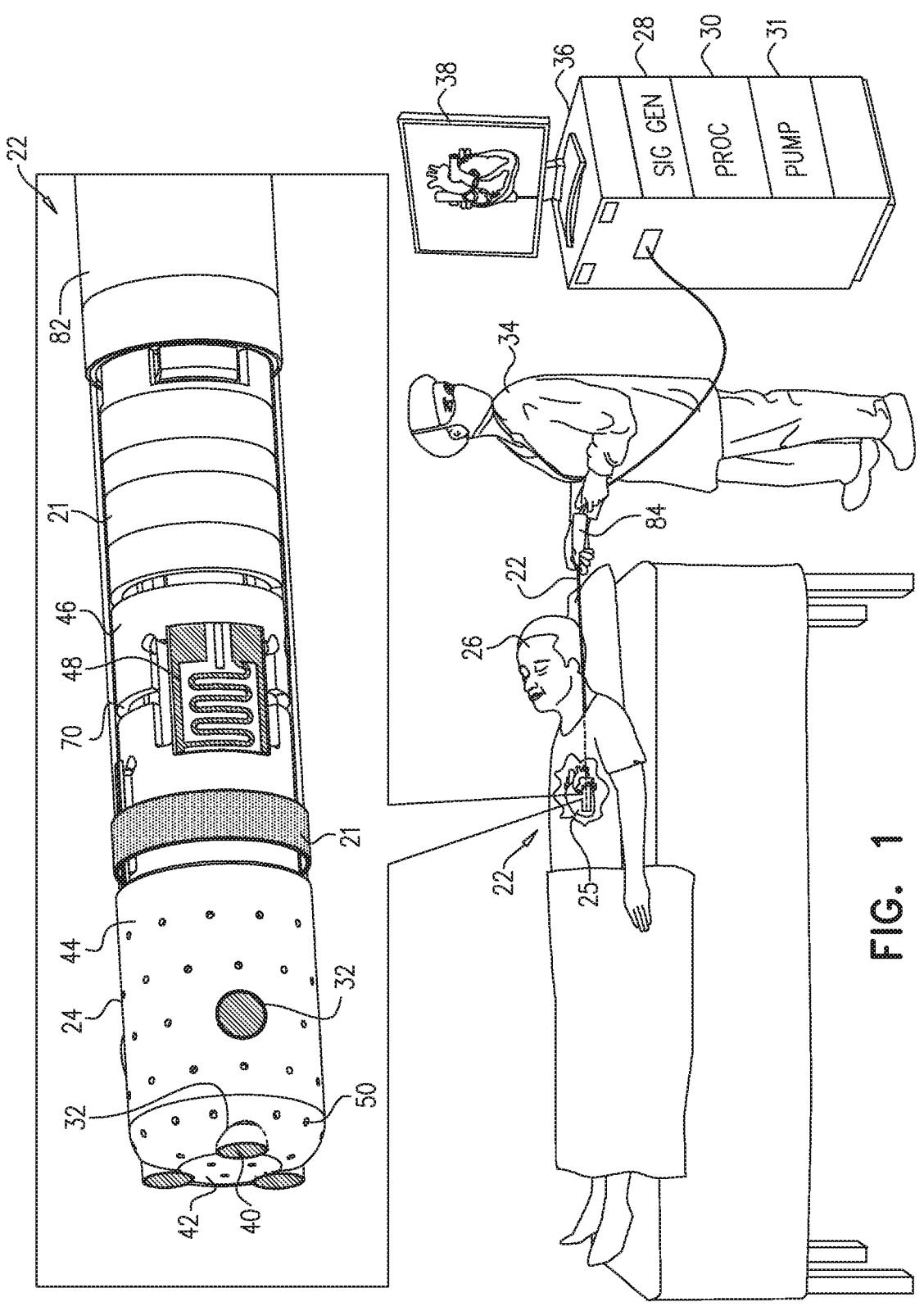
FIG. 1 is a schematic illustration of a procedure using an ablation catheter, in accordance with some embodiments of the present invention.

Embodiments described herein include an ablation catheter for use in ablating tissue, such as intracardiac tissue. The catheter comprises a tip electrode at the distal end of the catheter, which is used to deliver ablating signals to the tissue. The catheter further comprises a plurality of microelectrodes, which are coupled to at least one printed circuit board (PCB) disposed within the lumen of the catheter. The microelectrodes are fittingly situated within microelectrode apertures in the tip electrode. During the ablation procedure, the microelectrodes may be used to acquire signals from the tissue, in order to help assess the electrical activity of the tissue. These signals may be carried by the PCB to the proximal end of the catheter.

Advantageously, the microelectrodes, and the PCB to which they are coupled, serve a structural role, in addition to the functional role described above. In particular, the fit of the microelectrodes within the microelectrode apertures, and the attachment of the microelectrodes to the PCB, inhibits the tip electrode from migrating from the rest of the catheter, such that it may not be necessary to have a separate "safety wire" holding the tip electrode. Typically, a conduit, or other support, within the tip electrode supports the PCB, such that the microelectrodes do not migrate from the microelectrode apertures.

During the ablation procedure, it is typically desired to pass an irrigating fluid into the blood surrounding the catheter, in order (i) to draw heat from the ablating tip, and (ii) to help prevent blood clots from forming. Hence, the tip electrode is typically shaped to define a plurality of fluid apertures, for passage of an irrigating fluid therethrough. Advantageously, embodiments described herein allow for a large amount of heat exchange between the tip electrode and the irrigating fluid, by providing, for passage of the fluid, a narrow space between the PCB and the tip electrode, along the inner surface of the tip electrode. As the fluid is forced through this narrow space prior to exiting from the fluid apertures, a large amount of heat is absorbed from the tip electrode. In some embodiments, to pass the fluid through the narrow space, the fluid is deflected by the distal inner face of the tip electrode.

To increase the efficacy and/or safety of the ablation procedure, it is typically helpful to regulate the force applied to the tissue by the catheter. To this end, the catheter described herein typically further comprises a slotted tube, which is disposed within the lumen of the catheter, near the distal end of the catheter. A plurality of slots along the tube divide the tube into separate segments, each neighboring pair of the segments being spanned by a respective bridge. A plurality of strain gauges are coupled, respectively, to the bridges. As the catheter pushes against the tissue at the contact point between the tip electrode and the tissue, the force applied to the catheter by the tissue causes the bridges to bend. The strain gauges measure this bending, and output signals in response thereto. Based on these signals, the magnitude and direction of the force may be estimated, such that the force may be appropriately regulated.

Apparatus Description

Reference is initially made to FIG. 1, which is a schematic illustration of a procedure using an ablation catheter 22, in accordance with some embodiments of the present invention. FIG. 1 depicts a physician 34 using catheter 22 to perform an ablation of tissue within a heart 25 of a subject 26. Catheter 22 comprises a catheter shaft 82, at a distal end of which is disposed a tip electrode 24. During the ablation procedure, tip electrode 24 is inserted into heart 25. Tip electrode 24 is then brought into contact with the intracardiac tissue, and ablating signals are passed, via the tip electrode, into the tissue.

A console 36, which is connected to the ablation catheter via a catheter handle 84 at the proximal end of the catheter, includes a signal generator ("SIG GEN") 28, which generates the ablating signals, a processor ("PROC") 30, which receives and processes signals received from the distal end of the catheter, and a pump 31, which pumps irrigating fluid to the distal end of the catheter. During the procedure, anatomical information, and/or any other relevant information, may be displayed on a monitor 38.

Tip electrode 24 is shaped to define a plurality of micro-electrode apertures 32, within which, respectively, a plurality of microelectrodes 40 are fittingly situated. (Typically, the microelectrodes are electrically and thermally isolated from the tip electrode.) In general, any number of micro-electrode apertures 32—and hence, microelectrodes 40—may be located along the distal face 42 of the tip electrode, and/or the circumferential face 44 of the tip electrode. In some embodiments, for example, catheter 22 comprises six microelectrodes—three at distal face 42, and three at circumferential face 44, the latter three microelectrodes being spaced apart from each other by approximately 120 degrees. Each of the microelectrodes may either be flush with the outer surface of the tip electrode, or alternatively, may protrude from the outer surface. (Such protrusion may facilitate a more accurate temperature reading by a temperature sensor located beneath the microelectrode, as described below, by bringing the temperature sensor closer to the tissue from which the reading is acquired.) Upon the tip electrode being placed in contact with the tissue, the tip electrode passes an ablating signal into tissue, while the microelectrodes acquire intracardiac electrocardiogram (ECG) signals from the tissue. Alternatively or additionally, the microelectrodes may be used to pass current into the tissue for impedance measurements, which may be used, for example, for impedance-based location-sensing.

Typically, tip electrode 24 is further shaped to define a plurality of fluid apertures 50, which are configured to allow passage of a fluid therethrough. During the ablation procedure, while ablating signals are being passed into the tissue, an irrigating fluid is delivered to, and passed through, fluid apertures 50, as further described below. The fluid apertures are typically much smaller than the microelectrode apertures, and are typically located mostly (or entirely) along the circumferential face of the tip electrode, i.e., typically most, or all, of the fluid apertures pass through the circumferential face.

Typically, catheter 22 further comprises a slotted tube 46, which is typically situated at a distal portion of the catheter, such as immediately proximally to, and/or partly underneath, tip electrode 24. (For example, the proximal end of the tip electrode may slide over the distal portion of the tube.) As described in detail below, tube 46 is shaped to define one or more slots 70 at respective longitudinal positions along the tube, each of slots 70 separating between two respective segments of the tube, such that the segments are at least partly disconnected from each other. Each pair of neighboring segments is spanned by a bridge 74. One or more strain gauges 48 are coupled to bridges 74, each strain gauge 48 being configured to measure the strain in the bridge to which the strain gauge is coupled. As described above, these measurements may be used to estimate the force applied to the tissue by the catheter during the ablation procedure. Typically, slotted tube 46 is metallic; for example, the slotted tube may be manufactured from any suitable metallic alloy, such as nitinol.

Figure 5:
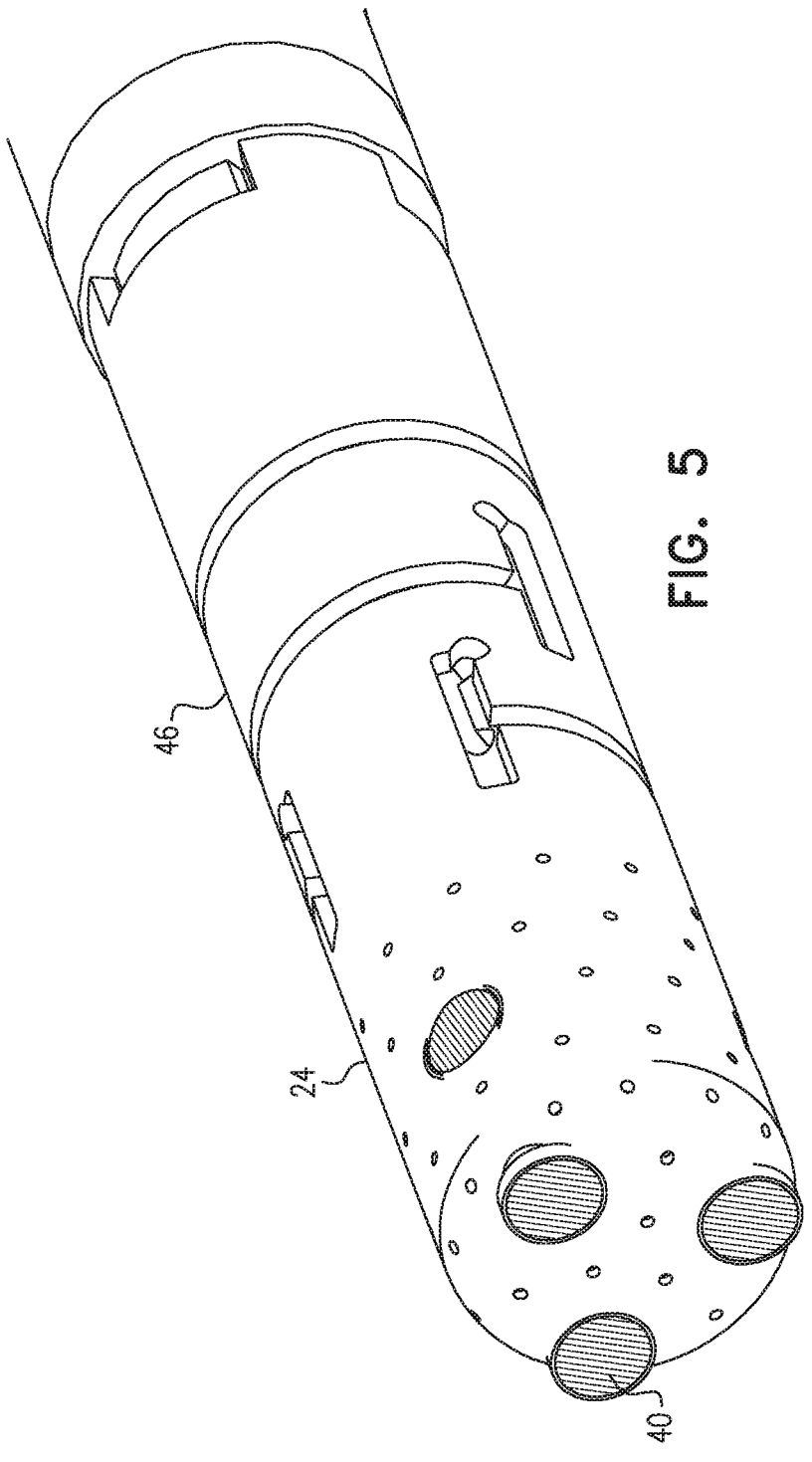
FIG. 5 is a schematic illustration of an ablation catheter, in accordance with some embodiments of the present invention.

Although, in FIG. 1, the slotted tube and strain gauge are seen through a transparent portion of the outer surface of the catheter, it is noted that the portion of the outer surface of the catheter that covers the slotted tube is not necessarily transparent. It is further noted that, in some embodiments, the slotted tube is not covered, such that the slotted tube itself constitutes part of the outer wall of the catheter, as shown in FIG. 5, which is described below.

In some embodiments, catheter 22 further comprises one or more ring electrodes 21 on the surface of the catheter. Ring electrodes 21 may be used, for example, for ECG-signal acquisition, or injection of current for impedance-based location-sensing.

Figure 2:
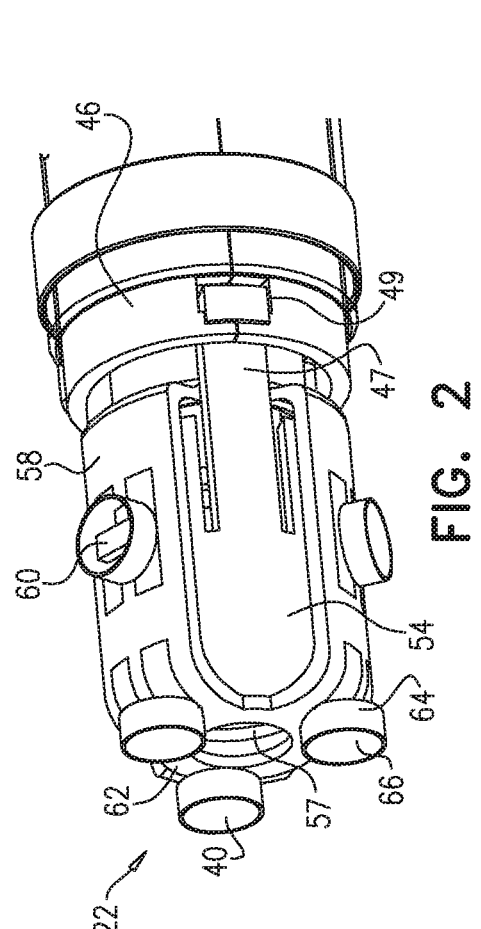
FIG. 2 is a schematic illustration of the distal end of a catheter, in accordance with some embodiments of the present invention.

Reference is now made to FIG. 2, which is a schematic illustration of the distal end of catheter 22, in accordance with some embodiments of the present invention. (In FIG. 2, tip electrode 24 is hidden, such that the components of the catheter underneath the tip electrode are visible.)

Typically, at least one flexible PCB 58 is disposed within the lumen of the catheter. For example, FIG. 2 shows a single PCB 58, comprising three splines that are folded over such that the splines extend proximally from the distal end 62 of PCB 58. PCB 58 typically runs through the lumen of the catheter, such that the PCB is covered by catheter shaft 82, i.e., the PCB is typically not exposed. In some embodiments, PCB 58 extends from the distal end of the catheter to catheter handle 84, and is directly coupled to the catheter handle. In other embodiments, the proximal end of PCB 58 is connected to a cable, and the cable is coupled to the catheter handle. In either case, the coupling of the PCB to the catheter handle—whether a direct coupling, or a coupling via a cable—anchors the PCB (and hence, the tip electrode, as further described below) to the catheter handle.

As shown in FIG. 2, microelectrodes 40 are coupled to the PCB, and the PCB carries signals from the microelectrodes to the proximal end of the catheter. In some embodiments, PCB 58 also carries signals to the distal end of the catheter. For example, PCB 58 may carry current, for injection into tissue, to ring electrodes 21 (FIG. 1). Alternatively or additionally, PCB 58 may carry signals, such as current signals for injection for impedance measurements, to the microelectrodes, and/or ablating signals to the tip electrode via an electrical coupling between tube 46 and tip electrode.

Typically, each microelectrode comprises a conducting element 66 and an isolating wall 64. Isolating wall 64, which is typically glued to PCB 58, surrounds conducting element 66, thus electrically- and thermally-isolating the conducting element from the tip electrode. Conducting element 66 is typically electrically coupled to PCB 58 (e.g., by being directly connected to the PCB), such that ECG signals detected by the conducting surface may be carried by the PCB from the distal end of the catheter. In some embodiments, as shown, each microelectrode is cylindrically shaped, whereby isolating wall has an annular shape, and the outer surface of conducting element 66, which forms the top of the cylinder, is circular. Typically, the diameter of the microelectrode apertures in the tip electrode is only slightly larger than that of the microelectrodes, such that the micro-electrodes fit snugly into the apertures. Alternatively or additionally, during the manufacture of catheter 22, the microelectrodes may be glued to, or otherwise fixed to, the respective perimeters of the microelectrode apertures. Thus, the microelectrodes are securely coupled to the tip electrode.

Typically, temperature sensors 60, such as thermistors, are also coupled to the PCB, and the PCB further carries signals from temperature sensors 60. Typically, each temperature sensor is located within a respective isolating wall 64, beneath the outer surface of a respective conducting element 66. (For clarity, in FIG. 2, the conducting element of one of the microelectrodes is hidden, revealing a temperature sensor 60.) In such embodiments, conducting elements 66 are thermally coupled to the temperature sensors (e.g., by contacting the temperature sensors), such that the conducting elements conduct heat from the tissue to the temperature sensors, thus facilitating the measuring of the tissue temperature by the temperature sensors.

Although the tip electrode is typically fastened to the remainder of the catheter (e.g., by being fastened to tube 46), a fallback securement mechanism for the tip electrode may be desired. Advantageously, as noted above, the PCB, together with the microelectrodes, serve as such a fallback securement mechanism, by anchoring the tip electrode to the remainder of the apparatus. For example, the tip electrode may be anchored to the catheter handle, by virtue of the PCB—which is attached to the microelectrodes, which are securely coupled to the tip electrode—being connected to the catheter handle. It may thus be unnecessary to attach a safety wire, or any other dedicated fallback securement mechanism, to the tip electrode. The PCB thus provides structural stability to the catheter, in addition to carrying signals to and/or from the distal end of the catheter.

In some embodiments, one or more of the microelectrodes at distal face 42 are oriented obliquely (e.g., at 45 degrees) with respect to distal face 42. Such an orientation further helps to anchor the tip electrode in place, by inhibiting the tip electrode from sliding distally.

Typically, PCB 58 is supported by a conduit 54, which, aside from supporting PCB 58 (and hence inhibiting the microelectrodes from retracting, i.e., sliding inward from the surface of the tip electrode into the lumen of the tip electrode), also allows passage of fluid therethrough. Conduit 54 is shaped to define a distal opening 57, i.e., an opening at the distal end of the conduit, through which, as further described below, irrigating fluid may pass. As shown in FIG. 2, conduit 54 may be coupled to slotted tube 46, e.g., via tabs 47 of the conduit that fit into complementary apertures 49 in the slotted tube.

Alternatively or additionally to conduit 54, PCB 58 may be supported by any other structure, such as an annular supporting structure, that prevents radially-inward migration of the microelectrodes.

Figure 3:
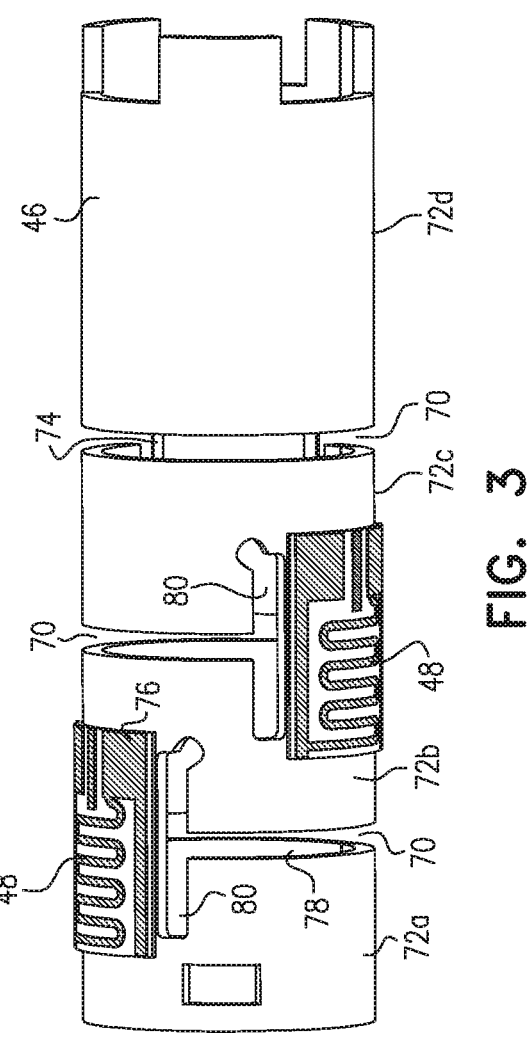
FIG. 3 is a schematic illustration of a slotted tube, in accordance with some embodiments of the present invention.

Reference is now made to FIG. 3, which is a schematic illustration of slotted tube 46, in accordance with some embodiments of the present invention. As described above, slotted tube 46 is shaped to define one or more slots 70, at respective longitudinal positions along the tube, which divide the tube into a plurality of segments. For example, in FIG. 3, three slots divide the tube into four segments—a first segment 72a, a second segment 72b, a third segment 72c, and a fourth segment 72d. Typically, the slotted tube is formed by laser-cutting the slots into an uncut tube.

Each of slots 70 typically includes, in addition to a circumferential portion 78 that passes circumferentially along the tube, two longitudinal portions 80 that pass longitudinally along the tube at respective ends of circumferential portion 78. (Longitudinal portions 80 thus "cut into" the segments.)

Between the two ends of each longitudinal portion 80 lies a respective bridge 74, which spans the pair of neighboring segments separated by the slot. In response to forces applied to the catheter, bridges 74 bend. Typically, each of the slots runs along a large majority of the circumference of the tube, such that each bridge 74 is relatively narrow. For example, each slot may be, circumferentially, between 315 and 345 degrees long (i.e., each slot may pass along 315-345 degrees of the circumference of the tube), such that bridge 74 is between 15 and 45 degrees wide. The relative narrowness of the bridges facilitates the bending of the bridges.

As shown in FIG. 3, strain gauges 48 are typically coupled to bridges 74, such that each strain gauge spans a respective pair of segments. (In FIG. 3, the rightmost strain gauge is not shown, due to this strain gauge being located at a portion of the tube that faces away from the viewer.) The bending of each bridge 74 causes a signal to be output by the strain gauge that is coupled to the bridge, the signal indicating the strain in the bridge. The signals from the strain gauges are carried, by PCB 58, to the proximal end of the catheter.

For example, each strain gauge shown in FIG. 3 comprises a resistor 76. As the shape of the strain gauge changes due to the strain in the bridge, the resistance of resistor 76 changes. Via PCB 58, a voltage may be applied across the strain gauge, such that the measured current flowing through the strain gauge indicates the change in resistance of the strain gauge, and hence, the strain in the bridge. Alternatively, a current may be applied across the strain gauge, such that the measured voltage across the strain gauge indicates the change in resistance of the strain gauge. This measured voltage or current is referred to herein as the "signal," output by the strain gauge, that indicates the strain in the bridge.

Based on the signals from strain gauges 48 that indicate the strain measurements, the force that is being applied to the catheter may be estimated. In particular, by placing three strain gauges at different respective circumferential positions along the tube, three separate, independent strain measurements may be obtained. Based on these three strain measurements, the direction of the force, in addition to the magnitude of the force, may be ascertained. For example, as shown, the three strain gauges may be spaced equiangularly along the tube, such that 120 degrees separates between respective middles of any two of the strain gauges.

In some embodiments, as shown, strain gauges 48 are coupled to the outer surfaces of the bridges. In such embodiments, connecting elements (not shown) may connect the strain gauges to the PCB disposed within the tube, such that the PCB may carry the signals from the strain gauges. In other embodiments, strain gauges 48 are coupled to the inner surfaces of the bridges. In such embodiments, the strain gauges may be mounted on the PCB.

Figure 4:
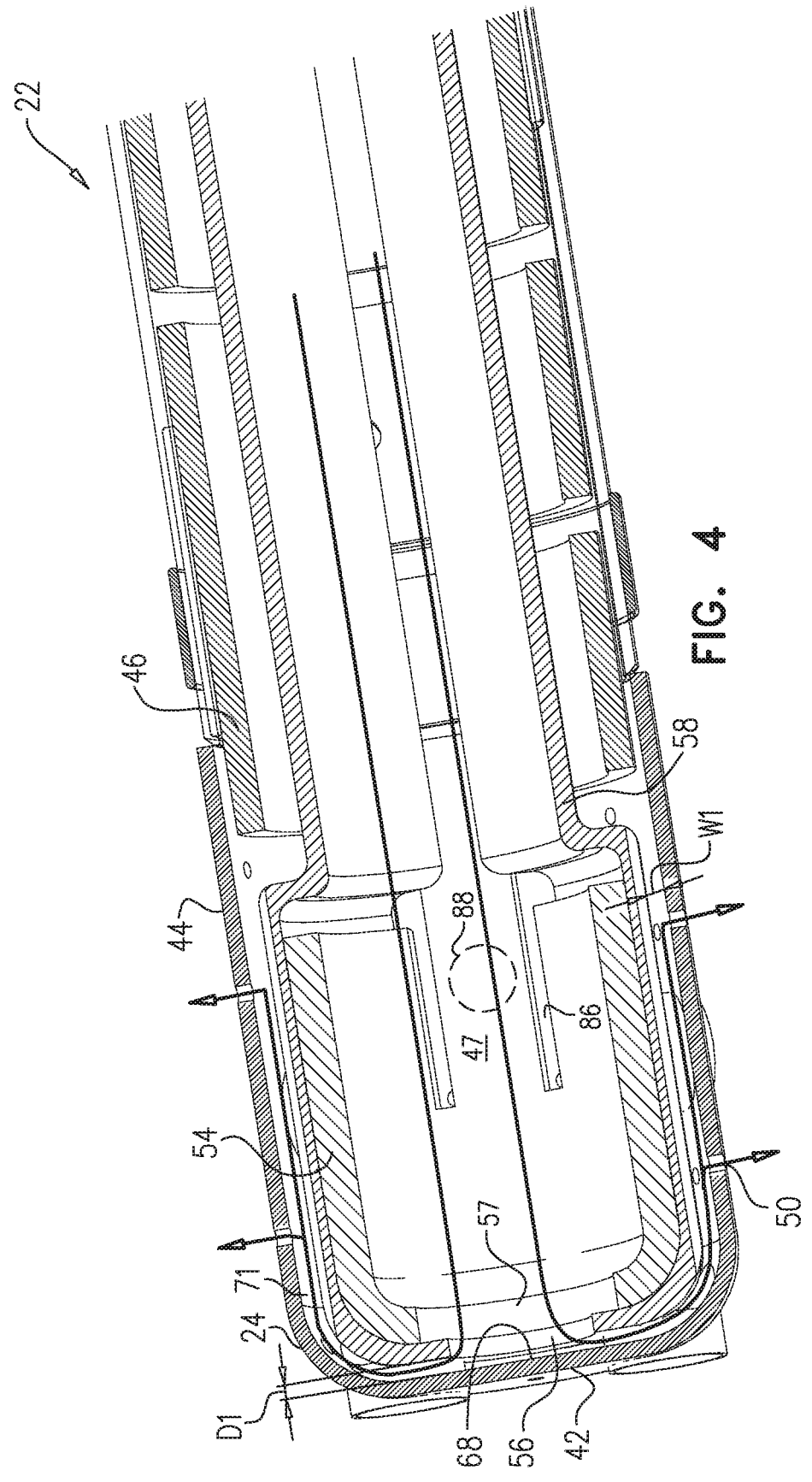
FIG. 4 is a schematic illustration of a longitudinal cross-section of the distal end of a catheter, in accordance with some embodiments of the present invention.

Reference is now made to FIG. 4, which is a schematic illustration of a longitudinal cross-section of the distal end of catheter 22, in accordance with some embodiments of the present invention.

As described above, during the ablation procedure, pump 31 delivers irrigating fluid to the distal end of the catheter. FIG. 4 shows an example flow pattern of this irrigating fluid, as the irrigating fluid approaches, and then passes through, tip electrode 24. First, the fluid passes through tube 46, and then through conduit 54. Next, the fluid passes through opening 57 of the conduit and through an opening 56 at the distal end of the PCB. The fluid thus reaches distal face 42 of the tip electrode, and is subsequently deflected, by the inner surface 68 of distal face 42, into a space 71 that lies between (i) the PCB and conduit, and (ii) the tip electrode. (Space 71 is typically situated primarily adjacent to circumferential face 44 of the tip electrode.) After flowing, through space 71, along the inner surface of the tip electrode, the fluid reach fluid apertures 50, and exits from the tip electrode via the fluid apertures.

Typically, the fluid, as it flows distally through the lumen of the catheter, is contained by the catheter, such that all, or at least a substantial majority of, the fluid reaches opening 57 of the conduit, and then flows proximally through space 71, as described above. In this regard, it is noted that any slots 86 adjacent to tab 47 are typically relatively narrow, such that relatively little fluid escapes from slots 86. It is further noted that any fluid that escapes through slots 70, between segments of tube 46, typically does not reach space 71; rather, the path of this fluid is blocked by tip electrode 24.

Notwithstanding the above, in some embodiments, catheter 22 comprises a fluid-delivery tube, which delivers fluid to the distal end of the catheter. For example, the distal end of such a fluid-delivery tube may be connected to the proximal end of conduit 54, such that fluid flows through the fluid-delivery tube to conduit 54, and then through conduit 54 as described above. Alternatively, for example, the distal end of such a fluid-delivery tube may be immediately proximal to (e.g., within 0.1 mm of) inner surface 68, such that the fluid reaches inner surface 68 immediately upon exiting the fluid-delivery tube.

In some embodiments, catheter 22 does not comprise conduit 54. In such embodiments, the portion of the PCB that is distal to tube 46 may be closed (i.e., the openings between the PCB splines may be closed), such that the PCB functions as a conduit, in that the fluid flows through the PCB to the distal face of the tip electrode.

Typically, the PCB and conduit are positioned within the tip electrode such that space 71 is relatively narrow. For example, the portion of the space that is between the PCB and the tip electrode may be less than 0.1 mm in the radial direction, i.e., the width W1 of the space, measured between the PCB and the inner surface of the tip electrode, may be less than 0.1 mm. (Assuming the thickness of the PCB is approximately 0.2 mm, this implies that the portion of the space between conduit 54 and the inner surface of the tip electrode may be less than 0.3 mm.) The narrowness of space 71 forces the fluid to flow near the inner surface of tip electrode 24, along a large portion of this surface, such that a relatively large amount of heat is transferred from the tip electrode to the fluid.

Typically, the majority of the fluid apertures are in the circumferential face of the tip electrode, rather than the distal face, such that relatively little fluid escapes from the catheter, prior to flowing through space 71. Thus, a relatively large amount of heat may be transferred from the tip electrode to the fluid. For example, in some embodiments, distal face 42 does not have any fluid apertures, such that all of the fluid is forced into space 71. Alternatively, some fluid apertures may be positioned within distal face 42.

Typically, distal opening 57 is positioned relatively close to distal face 42, e.g., within 0.3 mm of the distal face. Typically, the distal end of the conduit is flush with the distal end of the PCB, with distal opening 57 being aligned with distal opening 56 of the PCB. Thus, all of the fluid exiting through distal opening 57 is forced through distal opening 56, emerging from distal opening 56 within a small distance D1, which may be less than 0.1 mm, of distal face 42.

Were the conduit positioned more proximally, some of the fluid exiting from opening 56 might flow directly to the fluid apertures, without first flowing along the inner surface of the tip electrode. By positioning the conduit near the distal face, therefore, the fluid is forced to flow along the inner surface of the tip electrode, prior to exiting from the tip electrode.

As described above, FIG. 4 shows a flow pattern according to which the fluid flows, along the inner surface of the tip electrode, mainly in a proximal direction. Alternatively or additionally, the fluid may flow in the opposite longitudinal direction, i.e., the distal direction, along the inner surface of the tip electrode. For example, tabs 47, and/or other portions of conduit 54 (or of any other structure positioned within the tip electrode), may be shaped to define one or more circumferential (or "side") openings 88, such that the irrigating fluid flows through openings 88 into space 71, flows distally through space 71, and exits through the fluid apertures. (In such embodiments, the distal end of the conduit is typically closed, such that fluid does not flow directly to the distal face of the tip electrode.) In such embodiments, the majority, or all, of the fluid apertures may be located on the distal face of the tip electrode, such that most, or all, of the fluid forced into space 71 flows along most of the length of the tip electrode, prior to exiting from the tip electrode.

Reference is now made to FIG. 5, which is a schematic illustration of an ablation catheter, in accordance with some embodiments of the present invention. In the embodiment shown in FIG. 5, tip electrode 24 and tube 46 are formed from a single piece of material, e.g., a single piece of nitinol, such that the tip electrode is continuous with the tube. (Stated differently, in the embodiment of FIG. 5, the distal-most segment of tube 46 functions as the tip electrode.) This embodiment thus differs from previously-described embodiments, in which the tip electrode and the tube are manufactured separately, and are then physically and/or electrically coupled to one another. Advantages of such a design include simplicity of, and reduced cost of, manufacture.

It will be appreciated by persons skilled in the art that the present invention is not limited to what has been particularly shown and described hereinabove. Rather, the scope of embodiments of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. An apparatus, comprising:
(a) a catheter;
(b) an electrode tip located at a distal portion of the catheter;
(c) a printed circuit board (PCB) disposed within the electrode tip and comprising a distal tip defining an opening, the distal tip of the PCB being spaced proximally from a distal face of the electrode tip such that the PCB and the electrode tip cooperate to define a transversely extending gap between the PCB and the electrode tip, the opening defined by the distal tip of the PCB being in fluid communication with the transversely extending gap;
(d) a conduit extending within the electrode tip, the conduit in fluid communication with the opening defined by the distal tip of the PCB such that the conduit is configured to allow passage of fluid from the conduit through the opening defined by the distal tip of the PCB and into the transversely extending gap;
(e) a tube located at the distal portion of the catheter, the tube extending proximally relative to the electrode tip, the tube defining a tubular shape having a rounded exterior surface defining an outer circumference, the tube comprising:

(i) one or more partial circumferential slots cut in the tube at different longitudinal locations along a length of the tube, the one or more partial circumferential slots defining a plurality of segments of the tube that are partly disconnected from each other by the one or more partial circumferential slots, and (ii) a plurality of bridges comprising uncut portions of the tube, the plurality of bridges spanning respective neighboring pairs of the plurality of segments such that each of the plurality of bridges defines a continuous surface area between the respective neighboring pairs of the plurality of segments, each of the plurality of bridges being disposed at different respective circumferential positions along the tube and at different longitudinal positions along the tube such that each of the plurality of bridges is both longitudinally and radially offset from each other of the plurality of bridges; and (f) one or more strain gauges secured to the rounded exterior surface of the tube such that the one or more strain gauges are positioned along the outer circumference of the tube and thereby conform to the rounded exterior surface of the tube, each of the one or more strain gauges being coupled to a respective one of the plurality of bridges such that each of the one or more strain gauges is disposed at a different respective circumferential position along the outer circumference of the tube and at a different longitudinal position along the outer circumference of the tube and such that each of the one or more strain gauges is both longitudinally and radially offset from each other of the one or more strain gauges, and each of the one or more strain gauges being configured to output a signal indicative of strain in the respective one of the plurality of bridges in response to bending of the respective one of the plurality of bridges.

2. The apparatus according to claim 1, each of the one or more partial circumferential slots spanning between 315 and 345 degrees.

3. The apparatus according to claim 1, the tube being metallic.

4. The apparatus according to claim 1, the conduit supporting the PCB and being coupled to the tube.

5. The apparatus according to claim 4, the conduit comprising a plurality of tabs, and the conduit being coupled to the tube by virtue of the plurality of tabs fitting into complementary apertures in the tube.

6. The apparatus according to claim 1, the one or more strain gauges comprising three strain gauges.

7. A method, comprising:

using a tip electrode at a distal end of a catheter, passing an ablating signal into tissue, the catheter comprising:

the tip electrode at the distal end of the catheter;

a printed circuit board (PCB) disposed within the tip electrode and comprising a distal tip defining an opening, the distal tip of the PCB being spaced proximally from a distal face of the tip electrode such that the PCB and the tip electrode cooperate to define a transversely extending gap between the PCB and the tip electrode, the opening defined by the distal tip of the PCB being in fluid communication with the transversely extending gap;

a conduit extending within the tip electrode, the conduit in fluid communication with the opening defined by the distal tip of the PCB such that the conduit is configured to allow passage of fluid from the conduit through the opening defined by the distal tip of the PCB and into the transversely extending gap;

a tube having a rounded exterior surface defining an outer circumference, the tube comprising one or more partial circumferential slots cut in the tube at different longitudinal locations along a length of the tube, the one or more partial circumferential slots defining a plurality of segments of the tube that are partly disconnected from each other by the one or more partial circumferential slots, and a plurality of bridges comprising uncut portions of the tube, the plurality of bridges spanning respective neighboring pairs of the plurality of segments such that each of the plurality of bridges defines a continuous surface area between the respective neighboring pairs of the plurality of segments, each of the plurality of bridges being disposed at a different respective circumferential position along the tube and at a different longitudinal position along the tube such that each of the plurality of bridges is both longitudinally and radially offset from each other of the plurality of bridges; and while passing the ablating signal into the tissue, estimating a force applied to the tissue by the catheter, using a plurality of strain gauges, the plurality of strain gauges being secured to the rounded exterior surface of the tube such that the plurality of strain gauges conform to the rounded exterior surface of the tube, the plurality of strain gauges being coupled to the plurality of bridges such that each of the plurality of strain gauges is disposed at a different respective circumferential position along the outer circumference of the tube and at a different longitudinal position along the outer circumference of the tube and such that each of the plurality of strain gauges is both longitudinally and radially offset from each other of the plurality of strain gauges, the force estimate being based on strain measurements obtained at the different respective circumferential and longitudinal positions of the plurality of strain gauges on the outer circumference of the tube.

8. The method according to claim 7, further comprising, while passing the ablating signal into the tissue, passing a fluid through the conduit, through the opening defined by the distal tip of the PCB and into the transversely extending gap, and through a plurality of fluid apertures in the tip electrode.

9. The method according to claim 8, the passing the fluid further comprising passing the fluid through the tube.

10. The method according to claim 7, the estimating the force comprising:

using the plurality of strain gauges, outputting signals indicative of strain in the respective one of the plurality of bridges in response to bending of the plurality of bridges, and based on the signals, estimating the force.

11. The method according to claim 10, further comprising, using the PCB, carrying the signals to a proximal end of the catheter.

12. An apparatus, comprising:

(a) a catheter;

(b) an electrode assembly located at a distal portion of the catheter, the electrode assembly comprising:

(i) a tip electrode located at a distal portion of the catheter, the tip electrode comprising a plurality of fluid apertures, (ii) a printed circuit board (PCB) disposed within the tip electrode and comprising a distal tip defining an opening, the distal tip of the PCB being spaced proximally from a distal face of the tip electrode such that the PCB and the tip electrode cooperate to define a transversely extending gap between the PCB and the tip electrode, the opening defined by the distal tip of the PCB being in fluid communication with the transversely extending gap, (iii) a conduit extending within the tip electrode, the conduit in fluid communication with the opening defined by the distal tip of the PCB such that the conduit is configured to allow passage of fluid from the conduit through the opening defined by the distal tip of the PCB and into the transversely extending gap;

(c) a tube proximal of the electrode assembly, the tube comprising:

(i) a proximal end, (ii) a distal end, (iii) a rounded exterior surface defining an outer circumference, (iv) one or more partial circumferential slots cut in the tube at different longitudinal locations along a length of the tube, the one or more partial circumferential slots defining a plurality of segments arranged in a linear fashion between the proximal end and the distal end of the tube, the plurality of segments being partly disconnected from each other by the one or more partial circumferential slots, and (v) a plurality of bridges comprising uncut portions of the tube, the plurality of bridges spanning respective neighboring pairs of the plurality of segments such that each of the plurality of bridges defines a continuous surface area between the respective neighboring pairs of the plurality of segments, the plurality of bridges coupling the neighboring segments of the plurality of segments such that the plurality of bridges are linearly displaced from each other and circumferentially displaced from each other such that each of the plurality of bridges is both longitudinally and radially offset from each other of the plurality of bridges, the rounded exterior surface extending along the plurality of bridges; and (d) a plurality of strain gauges secured to the rounded exterior surface such that the plurality of strain gauges conform to a curvature of the rounded exterior surface and such that the plurality of strain gauges are positioned along the outer circumference of the tube, each strain gauge of the plurality of strain gauges being coupled to a respective bridge of the plurality of bridges such that the plurality of strain gauges are linearly displaced from each other and circumferentially displaced from each other on the outer circumference of the tube and such that each of the plurality of strain gauges is both longitudinally and radially offset from each other of the plurality of stain gauges, each strain gauge of the plurality of strain gauges being configured to output a signal indicative of strain in the respective one of the plurality of bridges in response to bending of the respective bridge of the plurality of bridges.

13. The apparatus of claim 12, the electrode assembly further comprising one or more microelectrodes connected to the tip electrode.

14. The apparatus of claim 1, each of the one or more partial circumferential slots comprising:

(A) a circumferential portion that passes partially circumferentially along the tube, (B) a first longitudinal portion extending longitudinally along the tube at a first circumferential end of the circumferential portion, and (C) a second longitudinal portion extending longitudinally along the tube at a second circumferential end of the circumferential portion, each bridge of the plurality of bridges extending circumferentially between the first and second longitudinal portions of a corresponding partial circumferential slot of the one or more partial circumferential slots.

15. The apparatus of claim 14, each strain gauge of the one or more strain gauges being circumferentially positioned between a corresponding first and second longitudinal portion of a corresponding partial circumferential slot of the one or more partial circumferential slots.

16. The apparatus of claim 12, each of the one or more partial circumferential slots comprising:

(A) a circumferential slot portion that passes partially circumferentially along the tube, (B) a first longitudinal slot portion extending longitudinally along the tube at a first circumferential end of the circumferential slot portion, the first longitudinal slot portion having a first distal segment extending distally in relation to the first circumferential end of the circumferential slot portion and a first proximal segment extending proximally in relation to the first circumferential end of the circumferential slot portion, and (C) a second longitudinal slot portion extending longitudinally along the tube at a second circumferential end of the circumferential slot portion, the second longitudinal slot portion having a second distal segment extending distally in relation to the second circumferential end of the circumferential slot portion and a second proximal segment extending proximally in relation to the second circumferential end of the circumferential slot portion.

17. The apparatus of claim 16, each bridge of the plurality of bridges being defined between a corresponding first longitudinal slot portion and a corresponding second longitudinal slot portion.

18. The method of claim 7, the conduit being coupled to the tube by one or more tabs extending proximally from the conduit fitting into complementary apertures in a distal portion of the tube.

19. The apparatus of claim 12, the conduit being coupled to the tube by one or more tabs extending proximally from the conduit fitting into complementary apertures in a distal portion of the tube.

* * * * *